US00PP18437P3

(12) United States Plant Patent
Olesen

(10) Patent No.: US PP18,437 P3
(45) Date of Patent: Jan. 15, 2008

(54) ROSE PLANT NAMED 'POULCAS020'

(50) Latin Name: *Rosa hybrida*
Varietal Denomination: Poulcas020

(75) Inventor: Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 11/337,268

(22) Filed: Jan. 19, 2006

(65) Prior Publication Data

US 2007/0169236 P1 Jul. 19, 2007

(51) Int. Cl.
*A01H 5/00* (2006.01)

(52) U.S. Cl. ..... Plt./151

(58) Field of Classification Search ..... Plt./151
See application file for complete search history.

*Primary Examiner*—Kent Bell
*Assistant Examiner*—Annette Para

(57) ABSTRACT

A new garden rose plant of the compact floribunda class which has abundant, red flowers and attractive foliage. This new and distinct variety has shown to be uniform and stable in the resulting generations from asexual propagation.

2 Drawing Sheets

Botanical classification: *Rosa* hybrid.
Variety denomination: 'Poulcas020'.

SUMMARY OF THE INVENTION

The present invention constitutes a new and distinct variety of garden rose plant which originated from a controlled crossing between the female seed parent 'Poulsyng', described and illustrated in U.S. Plant patent application Ser. No. 09/268,299 dated Mar. 16, 1999, now abandoned, and the male pollen parent, an unnamed seedling.

The two parents were crossed during the spring of 1997 and the resulting seeds were planted in a controlled environment in Fredensborg, Denmark. The new variety is named 'Poulcas020'.

The new variety may be distinguished from its female seed parent, 'Poulsyng', mainly by flower color. Flowers of 'Poulcas020' are red, while those of 'Poulsyng' are light pink.

The new variety may be distinguished from its male pollen parent by the following combination of characteristics:

1. While the pollen parent has 25 to 30 flower petals, 'Poulcas020' has 40 flower petals, 5 to 10 of which are petaloids.
2. The pollen parent has a general tonality of Red Group 46A, while 'Poulcas020' has a general tonality of Red Group 53A to Red-Purple Group 60A.

The objective of the hybridization of this rose variety was to create a new and distinct variety for garden use with unique qualities, such as:

1. Uniform and abundant red flowers;
2. Vigorous, but compact growth when propagated both as a budded rose and on its own roots;
3. Exceptional disease resistance; and
4. Glossy, attractive foliage.

This combination of qualities is not present in previously available commercial cultivars of this type, known to the inventors, and distinguish 'Poulcas020' from all other varieties of which we are aware.

As part of the rose development program, Mogens Nyegaard Olesen germinated the seeds from the aforementioned hybridization during winter of 1998 and conducted evaluations on the resulting seedlings in a controlled environment in Fredensborg, Denmark.

'Poulcas020' was selected in the spring of 1998 by the inventor as a single plant from the progeny of the aforementioned hybridization.

Asexual reproduction of 'Poulcas020' by traditional budding and rooted cuttings was first done by Mogens Nyegaard Olesen in the nursery in Fredensborg, Denmark in July, 1998. This initial and other subsequent asexual propagations conducted in controlled environments have demonstrated that the characteristics of 'Poulcas020' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poulcas020'. Specifically illustrated in the drawings:

FIG. 1.1; Open flower viewed from above and stem with cluster of partially open flower buds attached, showing branching, and the attachment of leaves, buds, and pedicels;

FIG. 1.2; Mature, bare stem showing thorns;

FIG. 1.3; Sepals, receptacle, and peduncle;

FIG. 1.4; Sepals, showing anthocyanic pigments;

FIG. 1.5; Flower petals, detached;

FIG. 1.6; Immature leaf;

FIG. 1.7; Mature leaf;

FIG. 2.1; Juvenile leaf showing hue and intensity of anthocyanic pigments;

FIG. 2.2; Juvenile stem showing thorns.

DETAILED DESCRIPTION OF THE VARIETY

The following is a description of 'Poulcas020', as observed in its growth in a field nursery in Jackson County, Oreg. Observed plants are 3 years of age, and were grown on *Rosa multiflora* understock. Color references are made using The Royal Horticultural Society (London, England) Colour Chart, 2001, except where common terms of color are used.

For a comparison, several physical characteristics of the rose variety 'Poultry', a rose variety from the same inventors described and illustrated in U.S. Plant patent application Ser. No. 10/976,225, are compared to 'Poulcas020' in Chart 1.

CHART 1

| | 'Poulcas020' | 'Poultry' |
|---|---|---|
| General Tonality of Flower Color | Red Group 53A to Red-Purple Group 60A | Red Group 53A |
| Flower Diameter | 50 to 60 mm | 50 to 80 mm |
| Basal Petal Spot Coloration - Upper Surface | Yellow Group 12B to 12C | Green-White Group 157B |

FLOWER AND FLOWER BUD

Blooming habit: Continuous.

Flower bud:

*Size.*—Upon opening, 22 mm in length from base of receptacle to end of bud. Bud diameter is normally 11 mm.

*Bud form.*—Broadened pointed ovate.

*Bud color.*—As sepals unfold, petals are Red-Purple Group 59A. At ¼ opening petals are Red Group 53A.

*Sepal inner surface.*—Color: Yellow-Green Group 144B with anthocyanic pigments the color of Greyed-Purple Group 183B. Surface: Medium pubescence observed.

*Sepal outer surface.*—Color: Yellow-Green Group 144A with anthocyanic pigments the color of Greyed-Purple Group 183B. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—25 mm (l)×6 mm (w).

*Receptacle.*—Texture: Smooth. Shape: Urn-shaped. Size: 10 mm (l)×9 mm (w). Color: Yellow-Green Group 144A with anthocyanic pigments the color of Greyed-Purple Group 183D.

*Peduncle.*—Length: 35 mm average. Diameter: 3 mm average. Color: Yellow-Green Group 144A with anthocyanic pigments the color of Greyed-Purple Group 183D.

Flower bud development: Flower buds are borne singly or in clusters of 5 to 9 flower buds per stem.

Flower bloom:

*Fragrance.*—Light floral to rose scent.

*Duration.*—As a field plant, the blooms have a duration of approximately 14 days. Petals fall cleanly away from plant after flowers have matured.

*Size.*—Flower diameter is 50–60 mm when open. Flower depth is 30 mm.

*Flower shape.*—In the early stages of flower development, the general shape is somewhat globular. As flowers mature, petals form a calathiform rosette, consisting of many slightly overlapping petals of different sizes.

*Shape of flower, side view.*—Upon opening, Upper portion: Flattened convex. Lower portion: Flat. After opening, Upper portion: Flat. Lower portion: Concave.

*Petalage.*—Under normal conditions, flowers have an average of 40 petals total, 5 to 10 of which are petaloids.

*Petal color.*—Upon opening, outer petals Upper surface: Red Group 53A to 45B. Lower surface: Red-Purple Group 61B to 60B. Upon opening, inner petals: Upper surface: Red Group 53A to 45B. Lower surface: Red-Purple Group 61B to 60B. Basal petal spots, upon opening: Upper surface: Yellow Group 12B to 12C. Lower surface: Yellow Group 12C. After opening, outer and inner petals Upper surface: Red Group 53A to 45B with intonations of Red-Purple Group 60A. Lower surface: Red-Purple Group 61B to 60B. Basal petal spots, after opening: Upper surface: Yellow Group 12B to 12C. Lower surface: Yellow Group 12C.

General tonality: On open flower Red Group 53A to Red-Purple Group 60A. No change in the general tonality at the end of the $10^{th}$ day.

Petals:

*Petal reflex.*—Outer petals reflex slightly.

*Margin.*—Entire and uniform. Occasional cleft at midpoint of the apex.

*Shape.*—Generally deltoid in shape. Apex: Rounded. Base: Acute.

*Size.*—Outer petals: 33 mm (l)×40 mm (w). Inner petals: 22 mm (l)×20 mm (w).

*Texture.*—Smooth.

*Thickness.*—Above Average.

Petaloids:

*Quantity.*—5 to 10.

*Shape.*—Elliptic to somewhat irregular.

*Color.*—Upper surface: Red Group 53A to 45B with intonations of Red-Purple Group 60A. Lower surface: Red-Purple Group 61B to 60B.

*Size.*—On average, 22 mm (l)×10 mm (w).

Reproductive organs:

*Pollen.*—None observed.

*Anthers.*—Size: 1 mm in length. Color: Greyed-Yellow Group 162A. Quantity: 60 to 70.

*Filaments.*—Color: Yellow Group 9C with intonations of Orange-Red Group 33B. Length: 7 mm.

*Pistils.*—Length: 6 to 7 mm. Quantity: 35 to 40.

*Stigmas.*—Color: Greyed-Yellow Group 160D.

*Styles.*—Color: Greyed-Green Group 192D.

*Hips.*—None Observed in the field nursery in Jackson County Oreg.

PLANT

Plant growth: Upright, moderately compact, and bushy. When grown as a budded field grown plant on *Rosa multiflora* understock, the height of the plant is 60 to 100 cm. Average spread is 60 cm.

Stems:

*Color.*—Juvenile growth: Yellow-Green Group 146C with anthocyanic intonations of Greyed-Purple Group 183A. Mature growth: Yellow-Green Group 146C.

*Length.*—On average, canes are 70 cm from the base of the plant to the flowering portion.

*Diameter.*—6 to 7 mm.

*Internodes.*—On mature canes, there is an average distance of 25 mm between nodes.

*Surface texture.*—Young wood: Smooth. Older wood: Smooth.

Prickles:

*Incidence.*—Normally, 11 thorns per 10 cm of stem.

*Size.*—Average length of thorns on mature stems is 11 mm.

*Shape.*—Upper surface is flat. Lower surface is concave.

*Color.*—Juvenile prickles: Greyed-Purple Group 183C. At the apex, prickles are occasionally Yellow-Green Group 146D. Mature prickles: Greyed-Yellow Group 162A with intonations of Greyed-Purple Group 183C.

Plant foliage: Normal number of leaflets leaves in middle of the stem: 5 to 7 leaflets.

*Compound leaf.*—On average, 105 mm (l)×80 (w).

*Quantity.*—3 leaves per 10 cm of stem on average.

*Color of mature foliage.*—Upper side: Yellow-Green Group 147A. Lower side: Yellow-Green Group 147B.

*Color of juvenile foliage.*—Upper side: Yellow-Green Group 146B with anthocyanin at margins the color of Greyed-Purple Group 183A. Lower side: Yellow-Green Group 144B with generalized anthocyanic intonations Greyed-Purple Group 183C.

Plants leaves and leaflets:

*Stipules.*—Size: 25 mm (l)×7 mm (w). Shape: Linear, slightly broad based with outward extending apecies. Margins: Finely serrated with many stipitate glands. Color: Yellow-Green Group 144B.

*Petiole.*—Length: On average, 15 mm. Diameter: On average, 2 mm.

*Upper surface.*—Color: Yellow-Green Group 146B with Greyed-Red Group 181C.

*Lower surface.*—Color: Yellow-Green Group 144A with light intonations of Greyed-Red Group 181C. Observations: Stipitate glands and small prickles observed on undersides.

*Rachis.*—Length: On average, 45 mm. Upper surface: Color: Yellow-Green Group 144A with overlay of Greyed-Purple 187A.

*Lower surface.*—Color: Yellow-Green Group 144B. Observations: Small prickles observed.

*Leaflet.*—Edge: Serrated. Size: Average size of the terminal leaflet on normal leaves is 40 mm (l)×35 mm (w). Shape: Generally rounded to elliptical. Base: Round. Apex: Mucronate. Texture: Smooth. Thickness: Average. Arrangement: Odd pinnate. Venation: Reticulate. Glossiness: Moderate glossy.

Disease resistance: Above average resistance to powdery and downy mildew, rust, black spot, and *Botrytis* under normal growing conditions in Jackson County, Oreg.

Cold hardiness: The variety 'Poulcas020' has been found to be cold tolerant to USDA Cold Hardiness Zone 6.

Heat tolerance: The variety has been found to be suitable for climate conditions found in the American Horticulture Society heat zone 7.

It is claimed:

1. A new and distinct variety of rose plant of the compact floribunda rose class named 'Poulcas020', substantially as illustrated and described herein, due to its abundant red flowers, glossy foliage, disease resistance, compact habit, suitability for production from softwood cuttings in pots, and extended period of bloom.

* * * * *

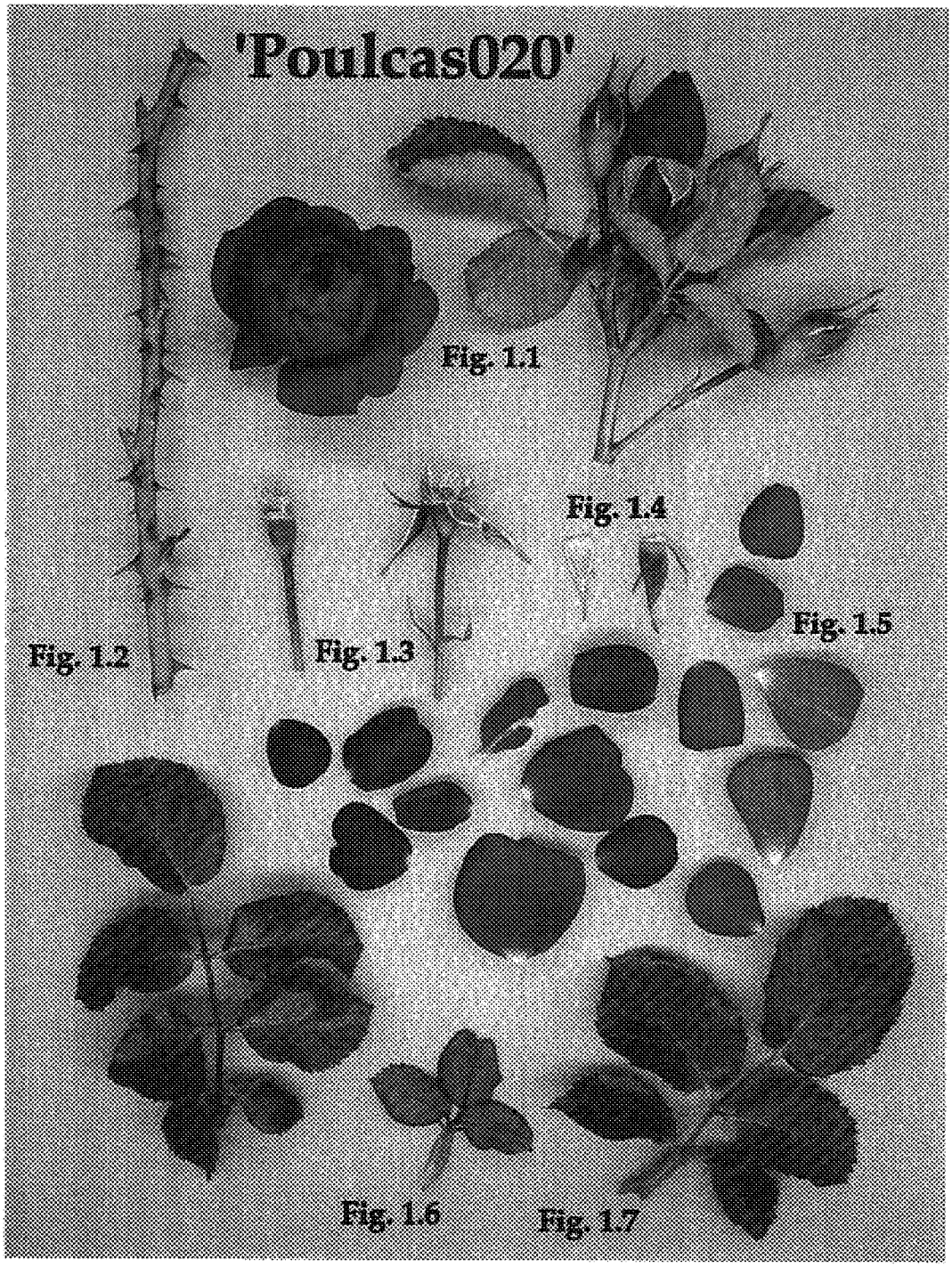
'Poulcas020'
Fig. 1.1
Fig. 1.2
Fig. 1.3
Fig. 1.4
Fig. 1.5
Fig. 1.6
Fig. 1.7

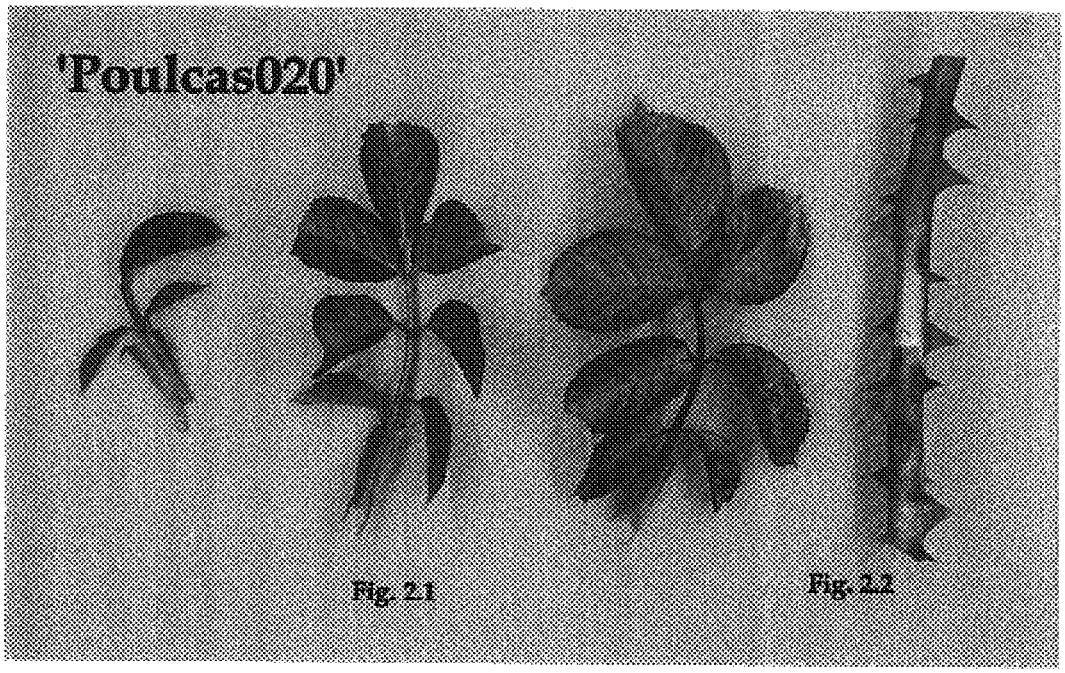
Fig. 2.1
Fig. 2.2